United States Patent [19]

Ladas et al.

[11] Patent Number: 5,100,648
[45] Date of Patent: Mar. 31, 1992

[54] COMPOSITION AND METHOD FOR CLEANING THE GUMS

[75] Inventors: Athanasios S. Ladas, Parsippany; Debbie L. Burnett-Davis, Stirling, both of N.J.; Ronald J. Sharpe, East Longmeadow, Mass.; Suzanne H. Ispentchian, Piscataway, N.J.

[73] Assignee: Pfizer Inc., New York, N.Y.

[21] Appl. No.: 728,004

[22] Filed: Jul. 1, 1991

Related U.S. Application Data

[60] Continuation of Ser. No. 460,455, Jan. 3, 1990, abandoned, which is a division of Ser. No. 173,833, Mar. 28, 1988, Pat. No. 4,895,720.

[51] Int. Cl.$^5$ ............................................... A61K 7/16
[52] U.S. Cl. ...................................................... 424/49
[58] Field of Search ....................................... 424/49-58

[56] References Cited

U.S. PATENT DOCUMENTS

| | | | |
|---|---|---|---|
| 4,428,929 | 1/1984 | Wicheta et al. | 424/49 |
| 4,627,972 | 12/1986 | Gioffre et al. | 424/49 |
| 4,631,184 | 12/1986 | Winyall et al. | 424/49 |
| 4,818,518 | 4/1989 | Gioffre et al. | 424/49 |
| 4,895,720 | 1/1990 | Ladas et al. | 424/49 |

*Primary Examiner*—Shep K. Rose
*Attorney, Agent, or Firm*—Peter C. Richardson; Paul H. Ginsburg; Robert F. Sheyka

[57] ABSTRACT

A composition for cleaning the gums comprising silica, water and a detergent, said composition having a RDA of less than 20.

5 Claims, No Drawings

COMPOSITION AND METHOD FOR CLEANING THE GUMS

This is a continuation of application Ser. No. 460,455, filed on Jan. 3, 1990 now abandoned which is a division of application Ser. No. 173,833, filed on Mar. 28, 1988, now U.S. Pat. No. 4,893,720.

BACKGROUND OF THE INVENTION

The present invention relates to a composition and method for cleaning the gums. Denture wearers should remove their dentures periodically, preferably twice daily, and brush their gums with a cleansing composition using a brush having soft bristles. A gel composition for such use is disclosed in U.S. Pat. No. 4,428,929 (the "'929 patent"), the disclosure of which is hereby incorporated herein by reference. The composition of the present invention provides formulations that are superior in appearance and "feel" to that of the gel of the '929 patent.

SUMMARY OF THE INVENTION

The present invention relates to a composition for cleaning the gums comprising silica, water and a detergent, said composition having a RDA (Radioactive Dental Abrasion, also referred to as Relative Dental Abrasion) of less than 20, more preferably, an RDA of less than 15, and most preferably an RDA of less than 10. In a preferred embodiment of the present invention, the composition also comprises sorbitol, polyethylene glycol, glycerin, and cellulose gum. The formulation may also comprise one or more of flavor, sweetener, coloring material and one or more preservatives. A preferred detergent for use in the composition of the present invention is sodium lauryl sulfate, a preferred silica is precipitated hydrated silica, a preferred sweetener is sodium saccharin, and a preferred preservative is sodium benzoate.

The compositions of the present invention are preferably gels. More preferably, they are gels that are visually clear, i.e., substantially translucent or transparent.

The present invention also relates to methods of cleaning the gums comprising applying to the gums the foregoing compositions. Such compositions are preferably applied by brushing the gums using a brush that has soft bristles.

DETAILED DESCRIPTION OF THE INVENTION

The silicas that may be used in the composition of the present invention are those silicas that are capable of functioning as thickening agents without causing the composition to have an unacceptable amount of abrasiveness for brushing the gums, i.e. their abrasiveness should be sufficiently low so that the RDA of the formulation will be less than 20. Silicas that are used as polishing agents in conventional toothpastes are likely to be too abrasive for use in the compositions of the present invention. An example of a type of silica that may be used in formulations of the present invention is a non-precipitated silica such as a silica aerogel. The preferred silica is a precipitated hydrated silica. Precipitated hydrated silicas are available from Degussa Corporation as Sipernat 22S (trademark) and Sipernat 22LS (trademark).

The RDA of the formulations of the present invention may be measured by the method disclosed by J. J. Hefferren in *J. Dent. Res.*, 563–573, (1976).

A more preferred formulation of the present invention comprises the following:
- (a) non-crystallizing sorbitol solution-about 45 to about 55 parts by weight;
- (b) water—about 15 to about 20 parts by weight;
- (c) precipitated hydrated silica—about 12 to about 16 parts by weight;
- (d) glycerin—about 9 to about 11 parts by weight;
- (e) polyethylene glycol—about 2 to about 4 parts by weight;
- (f) detergent (e.g., sodium lauryl sulfate)—about 2 to about 3 parts by weight
- (g) flavor—0 to about 1.5 parts by weight;
- (h) cellulose gum—about 0.4 to about 0.6 parts by weight; and
- (i) sweetener (preferably, sweetener that does not promote tooth decay and/or has a strong sweetening power, such as sodium saccharin)—about 0.2 to 0.3 parts by weight for sodium saccharin or an appropriate amount (i.e. having an equivalent sweetening effect) of another sweetener.

The foregoing formulation may also contain a preservative. The preservative should preferably be effective to prevent bacterial and fungal growth in the formulation for the desired shelf life and for a reasonable period of use by the consumer. A preferred perservative is sodium benzoate. When sodium benzoate is used as the preservative it would be used in an amount of about 0.08 to about 0.12 parts by weight. The foregoing formulation may also contain coloring material. Such coloring material would generally be used in an amount of about 0.8 to about 1.3 parts by weight of a 0.5 percent by weight aqueous solution.

A particularly preferred formulation of the present invention comprises the following:

| Ingredients | Parts By Weight |
| --- | --- |
| (a) non-crystallizing sorbitol solution | 50.00 |
| (b) water | 17.64 |
| (c) precipitated hydrated silica | 14.00 |
| (d) glycerin | 10.00 |
| (e) polyethylene glycol | 3.00 |
| (f) sodium lauryl sulfate | 2.40 |
| (g) flavor | 1.00 |
| (h) cellulose gum | 0.50 |
| (i) sodium saccharin | 0.25 |
| (j) sodium benzoate | 0.10 |
| (k) coloring material (0.50% by weight aqueous solution) | 1.11 |

In the foregoing formulations, the preferred precipitated hydrated silica is Sipernat 22S (trademark), Sipernat 22LS (trademark), or a mixture of such silicas. More preferably, the precipitated hydrated silica is a mixture of 11 parts by weight Sipernat 22S and 3 parts by weight Sipernat 22LS.

In the foregoing formulations, the preferred polyethylene glycol is PEG-6-32 (also known as Carbowax 1450 (trademark)), available from Union Carbide Corporation.

In the foregoing formulations, the preferred coloring material is a mixture of 0.68 parts by weight of D & C yellow #10 (0.50% by weight aqueous solution) and 0.43 parts by weight of FD & C Green #3 (0.50% by weight aqueous solution).

As used herein, the term non-crystallizing sorbitol solution refers to an aqueous solution that contains at least about 45 percent by weight sorbitol, at least about 20 percent by weight maltitol, and at least about 29 percent by weight water. This solution does not crystallize at 0° C., while USP Sorbitol crystallizes at about 25° C. The preferred material is LIPONIC 70-NC (trademark) available from Lipo Chemicals, Inc. of Paterson, N.J. The latter material contains 29-30 percent by weight water, 46-55 percent by weight sorbitol, 1-1.5 percent total sugars (primarily maltose), the balance being predominantly maltitol (a dimer of sorbitol) with a minor amount of higher molecular weight sugar alcohols.

A sorbitol solution containing about 60 to about 70 percent by weight sorbitol, preferably about 64 to about 70 percent by weight sorbitol and the remainder water (said solution preferably consisting essentially of sorbitol and water), may be substituted for the aforementioned non-crystallizing sorbitol solution in the formulations of the present invention. Other sweeteners that form viscous solutions, such as corn syrup or glucose, may also be substituted for the non-crystallizing sorbitol solution in the formulations of the present invention.

The compositions of the present invention may conveniently be packaged in a lined aluminum tube or in a plastic laminated tube. Such tubes are commonly used for oral care products such as toothpastes. When the composition of the present invention is used to clean the gums, an amount of gel that is about 1 to 2 centimeters in length is squeezed out of a conventional tube on to the surface of a brush having soft bristles and the brush is then applied to the gums. One should be careful to use bristles that are sufficiently soft so that they will not irritate the gums. The bristles of the brush are desirably made from a soft plastic such as polyethylene. A blend of high and low density polyethylenes that will give a desired combination of stiffness and softness may be used. The brush used for cleaning the gums may have bristles protruding from one surface of the brush head or two opposing surfaces of the brush head. Alternatively, the bristles may protrude from all surfaces of the brush head as shown in U.S. Pat. No. 4,328,604, the disclosure of which is hereby incorporated herein by reference.

It will be understood that the method of the present invention is also applicable to cleaning other oral tissues in addition to the gums but other than the teeth and that such cleaning is included within the scope of the invention.

The following Example illustrates the formulations of the present invention:

EXAMPLE 1

Oral Gum Cleaner

The ingredients set forth below were combined as described below:

| Ingredients | % by weight |
| --- | --- |
| LIPONIC 70-NC (trademark) (sorbitol solution) | 50.00 |
| Water | 17.64 |
| Silica | 14.00 |
| Glycerin | 10.00 |
| PEG-6-32 (Polyethylene Glycol) | 3.00 |
| Sodium Lauryl Sulfate | 2.40 |
| Flavor | 1.00 |
| Cellulose Gum | 0.50 |

| Ingredients | % by weight |
| --- | --- |
| Sodium Saccharin | 0.25 |
| Sodium Benzoate | 0.10 |
| D + C Yellow #10 (0.50% aqueous) | 0.68 |
| FD + C Green #3 (0.50% aqueous) | 0.43 |
| | 100.00 |

1. Melt the PEG-6-32 (polyethylene glycol) and add it to the previously heated LIPONIC 70-NC (trademark) sorbitol solution in a kettle (kettle A). Mix until homogeneous, maintaining the temperature at 70° C.
2. In a second kettle, disperse the cellulose gum in the glycerin. Mix until a uniform dispersion is obtained.
3. Add the cellulose gum and glycerin mixture prepared in step 2 to kettle A at 70° C. and slowly agitate for 5 minutes.
4. Combine the sodium saccharin and sodium benzoate in the water and mix at 70° C. Mix the yellow and green dyes into the resulting solution.
5. Add the solution prepared in step 4 to kettle A and mix with slow agitation at 70° C. until a uniform mixture is attained. Disperse the silica into the resulting mixture and mix at 70° C. until a smooth consistency is attained. Lower the temperature to 40° to 50° C. and then add the flavor, mixing until homogeneous. Dissolve the sodium lauryl sulfate in water and add the solution to the gel, mixing until homogeneous. Then deaerate the gel.

EXAMPLE 2

The radioactive dentin abrasion (RDA) levels of the Oral Gum Cleaner of Example 1, a conventional dentifrice (Advanced Formula Crest (trademark)), and water were determined as described below.

Procedure

The procedure used was the ADA recommended procedure (J. J. Hefferren, *J. Dent. Res.*, 563-573 (1976)) for determination of dentifrice abrasivity. The dentin specimens (8) were irradiated in a neutron flux in accordance with the ADA recommended procedure. The specimens were then mounted in methylmethacrylate so they would fit in a V-8 cross-brushing machine. The specimens were brushed for a 6000 stroke, precondition run using a slurry consisting of 10 g ADA reference material (calcium pyrophosphate) and 50 ml of a 0.5% carboxymethyl/cellulose/10% glycerin solution. The brushes used were those specified by the ADA recommended procedure, and brush tension was 150 g.

Following the precondition run, the test was performed using the specified sandwich design as follows:

| Run | Slurry | |
| --- | --- | --- |
| 1 | ADA Reference Material | (10 g/50 ml) |
| 2 | Oral Gum Cleaner | (25 g/40 ml) |
| 3 | ADA Reference Material | (10 g/50 ml) |
| 4 | Advanced Formula Crest (trademark) | (25 g/40 ml) |
| 5 | ADA Reference Material | (10 g/50 ml) |
| 6 | Tap Water | (50 ml) |
| 7 | ADA Reference Material | (10 g/50 ml) |

Three ml aliquotes were then removed from each slurry, dried and counted for radiation using a geiger counter. The pre and post net CPM (counts per minute) of the ADA reference material for each test slurry was then calculated and averaged to use in the calculation of RDA for each test material. The ADA material was assigned a value of 100 and its ratio to each test material was calculated.

Correction factors were prepared by adding 1 ml of a radioactive solution and 1 ml of a neutralizing solution to slurries of the test materials and of the ADA reference material. Aliquots of these slurries were taken and dried along with the test slurry aliquots. They were similarly counted at the same time as the test aliquots. The net CPM of the ADA reference material correction factor aliquot was then divided by the net CPM of each test material correction factor aliquot. The resulting number was the correction factor for that specific slurry. The correction factor was then applied to the mean RDA value for the respective group.

Results

The results are summarized in Table 1. As shown, the dentifrice slurry produced significantly more abrasion to dentin than did water or the Oral Gum Cleaner.

Conclusion

The Oral Gum Cleaner is not significantly more abrasive to dentin than is water.

TABLE 1

| RDA VALUES | | | |
| --- | --- | --- | --- |
| | Oral Gum Cleaner | AF Crest | Water |
| Specimen Number | | | |
| 1 | 6.79 | 90.40 | 7.97 |
| 2 | 6.79 | 92.97 | 11.97 |
| 3 | 7.31 | 86.88 | 8.36 |
| 4 | 7.31 | 85.95 | 10.10 |
| 5 | 7.04 | 91.62 | 10.00 |
| 6 | 6.26 | 96.31 | 11.78 |
| 7 | 6.64 | 94.69 | 9.24 |
| 8 | 7.24 | 89.54 | 11.01 |
| Raw Mean Score | 6.92 | 91.04 | 10.05 |
| ± S.E.M. | 0.13 | 1.28 | 0.52 |
| Self Absorption Correction Factor | 1.11 | 1.21 | 0.60 |
| Corrected Mean Score | 7.68 | 110.16 | 6.03 |
| ± S.E.M. | 0.14 | 1.55 | 0.31 |

We claim:

1. A gum cleaning gel composition for denture wearers, and having an RDA of less than 20, said composition consisting essentially of:
   (a) about 45 to about 55 parts by weight of (1) an aqueous sorbitol solution comprising about 60 to about 70 percent by weight sorbitol or (2) a non-crystallizing sorbitol solution comprising at least about 45 percent by weight sorbitol, at least about 20 percent by weight maltitol, and at least about 29 percent by weight water;
   (b) about 15 to about 20 parts by weight of water;
   (c) about 12 to about 16 parts by weight of precipitated hydrated silica;
   (d) about 9 to about 11 parts by weight glycerin;
   (e) about 2 to about 4 parts by weight polyethylene glycol;
   (f) about 2 to about 3 parts by weight of detergent;
   (g) 0 to about 1.5 parts by weight of flavor;
   (h) about 0.4 to about 0.6 parts by weight of cellulose gum; and
   (i) about 0.2 to about 0.3 parts by weight of sodium saccharin or an equivalent amount of another sweetener.

2. The composition of claim 1, said composition also comprising an effective amount of a preservative, coloring material or both.

3. The composition of claim 2, said preservative being present in an amount of about 0.08 to about 0.12 parts by weight.

4. The composition of claim 3, said coloring material being present in an amount of about 0.8 to about 1.3 parts by weight of a 0.5 percent by weight aqueous solution.

5. The gum cleaning gel composition for denture wearers, and having an RDA of less than 20, said composition consisting essentially of:
   (a) 50.00 parts by weight non-crystallizing sorbitol solution comprising at least about 45 percent by weight sorbitol, at least about 20 percent by weight maltitol, and at least about 29 percent by weight water;
   (b) 17.64 parts by weight water;
   (c) 14.00 parts by weight precipitated hydrated silica;
   (d) 10.00 parts by weight glycerin;
   (e) 3.00 parts by weight polyethylene glycol;
   (f) 2.40 parts by weight sodium lauryl sulfate;
   (g) 1.00 parts by weight flavor;
   (h) 0.50 parts by weight cellulose gum;
   (i) 0.25 parts by weight sodium saccharin;
   (j) 0.10 parts by weight sodium benzoate; and
   (k) 1.11 parts by weight of a 0.50 percent by weight solution of coloring material.

* * * * *